(12) United States Patent
Khraiche et al.

(10) Patent No.: US 9,381,355 B2
(45) Date of Patent: Jul. 5, 2016

(54) ULTRA-HIGH PHOTOSENSITIVITY VERTICAL NANOWIRE ARRAYS FOR RETINAL PROSTHESIS

(75) Inventors: Massoud L. Khraiche, San Diego, CA (US); Gabriel Silva, Del Mar, CA (US); Gert Cauwenberghs, San Diego, CA (US); Yu-Hwa Lo, San Diego, CA (US); Deli Wang, San Diego, CA (US); William Freeman, Del Mar, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 487 days.

(21) Appl. No.: 13/806,089

(22) PCT Filed: Jun. 21, 2011

(86) PCT No.: PCT/US2011/041293
§ 371 (c)(1),
(2), (4) Date: Jun. 28, 2013

(87) PCT Pub. No.: WO2011/163262
PCT Pub. Date: Dec. 29, 2011

(65) Prior Publication Data
US 2014/0128972 A1 May 8, 2014

Related U.S. Application Data

(60) Provisional application No. 61/356,655, filed on Jun. 21, 2010.

(51) Int. Cl.
*A61N 1/36* (2006.01)
*A61N 1/05* (2006.01)
(Continued)

(52) U.S. Cl.
CPC .............. *A61N 1/36046* (2013.01); *A61F 2/14* (2013.01); *A61N 1/0543* (2013.01); *A61L 27/18* (2013.01);
(Continued)

(58) Field of Classification Search
CPC .............. A61F 2/14; A61F 2/141; A61F 9/08; A61L 2400/12; A61N 1/36046; A61N 1/0543
See application file for complete search history.

(56) References Cited

U.S. PATENT DOCUMENTS 6,038,480 A 3/2000 Hrdlicka et al.
6,389,317 B1 5/2002 Chow et al.
(Continued)

OTHER PUBLICATIONS

Dayeh, S.A., et al., "Advances in the synthesis of InAs and GaAs nanowires for electronic applications", Nano Today, Jul. 5, 2009, vol. 4, pp. 347-358.
(Continued)

*Primary Examiner* — Howie Matthews
(74) *Attorney, Agent, or Firm* — Eleanor Musick; Musick Davison LLP

(57) ABSTRACT

A prosthetic retina for implantation in an eye having a defective retina is formed from an array of nanowires having a predetermined spatial distribution, density, size and shape implanted in close proximity to the retina. An electrical conductor is formed at a first end of all nanowires in the array of nanowires and placed in contact with a bias source which biases the array. A plurality of electrodes is located on a second end of each of one nanowire or a bundle of nanowires in the array. Each nanowire produces a photocurrent at a corresponding electrode in response to detection of light impinging on the array of nanowires and the photocurrent stimulates one or more neurons adapted for visual perception. In the preferred embodiment, the predetermined spatial distribution mimics a distribution of rods and cones in a normal eye.

20 Claims, 14 Drawing Sheets

(51) Int. Cl.
  *A61F 2/14* (2006.01)
  *A61L 27/18* (2006.01)
  *H01L 31/0352* (2006.01)
(52) U.S. Cl.
  CPC .......... *A61L 2400/12* (2013.01); *A61L 2430/16* (2013.01); *H01L 31/035227* (2013.01); *H01L 31/035236* (2013.01)

(56) References Cited

U.S. PATENT DOCUMENTS

| | | | |
|---|---|---|---|
| 7,006,873 | B2 | 2/2006 | Chow et al. |
| 7,139,612 | B2 | 11/2006 | Chow et al. |
| 7,494,840 | B2 | 2/2009 | Zhang et al. |
| 8,000,000 | B2 | 8/2011 | Greenbrg et al. |
| 2002/0074227 | A1 | 6/2002 | Nisch et al. |
| 2002/0161417 | A1 | 10/2002 | Scribner |
| 2003/0032946 | A1 | 2/2003 | Fishman et al. |

OTHER PUBLICATIONS

Dayeh, S.A., et al., "Integration of vertical InAs nanowire arrays on insulator-on-silicon for electrical isolation", Applied Physics Letters, Nov. 20, 2008, vol. 93, 203109-1 to 203109-3.

Fan, Z., et al., "Large-scale, heterogeneous integration of nanowire arrays for image sensor circuitry", PNAS, Aug. 12, 2008, vol. 105, No. 32, pp. 11066-11070.

Kim, H., et al., "Fabrication of Vertical Silicon Nanowire Photodetector Arrays using Nanoimprint Lithography", Advanced Fabrication Technologies for Micro/Nano Optics and Photonics III, ed. Schoenfeld, W.V. et al., Proc. of SPIE, 2010, vol. 7591, 759106-1 to 759106-7.

Okugawa, A., et al., "Heterogeneous Integration of Vapor-liquid-solid Grown Silicon Microprobe Arrays (111) and MOSFETS (100) using Silicon on Insulator Substrate", Proceedings of the IEEE Micro Electro Mechanical Systems (IEEE-MEMS) Conference 2010, Hong Kong, Jan. 2010, pp. 372-375.

Silva, G.A., "Neuroscience nanotechnology: progress, opportunities and challenges", Nature Reviews Neuroscience, Jan. 2006, vol. 7, pp. 65-74.

Soci, C., et al., "Nanowire Photodetectors", Journal of Nanoscience and Nanotechnology, 2010, vol. 10, pp. 1-20.

Sun, K., et al., "Compound Semiconductor Nanowire Solar Cells", IEEE Journal of Selected Topics in Quantum Electronics, 2011, 17(4), pp. 1033-1049.

Wei, W., et al., Direct Heteroepitaxy of Vertical InAs Nanowires on Si Substrates for Broad Band Photovoltaics and Photodetection, Nano Letters, 2009, vol. 9, No. 8, pp. 2926-2934.

Xiang, B., et al., "Rational Synthesis of p-Type Zinc Oxide Nanowire Arrays Using Simple Chemical Vapor Deposition", Nano Letters, 2007, vol. 7, No. 2, pp. 323-328.

Zhang, A., et al., "Silicon nanowire detectors showing phototransistive gain", Applied Physics Letters, 2008, vol. 93, 121110-1 to 121110-3.

EP 11798773.5 Extended European Search Report, Nov. 11, 2013, 5 pages.

PCT/US2011/041293 International Search Report and Written Opinion, Feb. 28, 2012, 10 pages.

ULTRA-HIGH PHOTOSENSITIVITY VERTICAL NANOWIRE ARRAYS FOR RETINAL PROSTHESIS

RELATED APPLICATIONS

The present application claims the benefit of the priority of U.S. Provisional Application No. 61/356,655 filed Jun. 21, 2010, the disclosure of which is incorporated herein by reference in its entirety.

FIELD OF THE INVENTION

The present invention is directed to a retinal implant for restoring vision to patients suffering retinal disease or degeneration. More specifically, the invention is directed to a nanoengineered retinal prosthesis.

BACKGROUND OF THE INVENTION

Damage to, or loss of, photoreceptors (PRs) in the eye, and/or damage to layers of the retina that prevents PR transmission to the brain, can lead to blindness. Photoreceptors detect light and stimulate downstream neurons in the retina. Around 1 million people in the United States alone suffer profound vision loss, with another 2.4 million having some degree of visual impairment. As the U.S. population continues to age, it is likely that the total number of affected individuals will increase, possibly by up to 50% by 2020, especially given the dramatic rise in type II diabetes. In recent years, age-related macular degeneration (AMD) the leading cause of vision loss in the elderly, has been successfully treated in many patients with intravitreal injections of LUCENTIS® (ranibizumab) or AVASTIN® (bevacizumab). Such drugs can require regular, e.g., monthly, injections to maintain the improvement, costing tens of thousand of dollars annually. In addition, some studies have brought into question the safety of long term treatment with these drugs, finding that accumulation of the drug in higher doses can result in destruction of PRs. Other forms of neural blindness, such as Retinitis Pigmentosa and Stargardt Disease, cannot currently be treated by any available means.

A number of research projects have been undertaken to develop a retinal implant capable of restoring vision to patients suffering retinal diseases. Retinal, cortical and optic nerve visual prostheses use microfabricated electronic components to stimulate neural circuitry that is still available despite whatever neural damage has caused blindness. This approach is attractive in that prostheses can directly stimulate surviving nerve cells and uses the functionality of the remaining, largely intact retinal neuronal circuitry. However, despite decades of research, visual prostheses have not advanced beyond early clinical trials and have not yet produced a level of vision that has been demonstrated to improve the ability of patients to perform visual tasks related to daily activities.

The current state of the art for retinal prosthesis utilizes a camera to capture the image and then relay the neural stimulation parameters to a microelectrode array (MEA) implanted in proximity to retinal neurons. The MEA consists of metal electrodes of diameters on the order of 30 µm, which are embedded into a flexible material. This type of image acquisition and stimulation is being used by two leading groups in retinal implants—Second Sight, Inc. (Sylmar, Calif.), which target epi-retinal implant locations, and the Boston retinal implant project, which targets a sub-retinal implant location. The epi-retinal approach places electrodes in the vitreous fluid, attached to the surface of the retina, while the subretinal approach places electrodes on the outside of retina, wedged between the photoreceptors and the retinal pigment epithelium. The retina section in FIG. 1 shows the electrode positions for the two types of retina prostheses.

The number of electrodes required to yield various levels of visual acuity has been estimated to be within the range of 256 to 625 electrodes, which theoretically might yield best visual acuity of 20/240 and 20/30, respectively. The high density of ganglion cells in the retina suggests that a greater number of stimulating electrodes could be implanted in a given area. However, the number of electrodes required depends on the ability of the materials to safely transmit charge and on the proximity of the target tissue to those electrodes. The current technology is not yet capable of restoring vision to a level that is sufficient for patients to lead an independent life and perform regular daily activities.

The barriers to restoring vision to the blind are significant. In addition to biomaterial issues such as toxicity, tissue encapsulation and cellular/immune responses that might be triggered by foreign materials, an electrical prosthesis must also provide long-term stability of the metal electrodes while minimizing any tissue damage that occurs as a result of the electrical stimulation. Induced tissue damage will reduce the excitability of the tissue and limit the potential for vision restoration. The potential biocompatibility and long-term functional stability of a retinal prosthesis are further complicated by ongoing anatomical and physiological changes that inevitably occur within the retina in patients with retinitis pigmentosa, the primary disease that has been targeted by early visual prosthetic implantations.

As is known in the art, when particles of materials are created with dimensions of around 1-10µ, the material's properties change. As used herein, a "nanomaterial" is a material in which quantum effects rule the behavior and properties of particles. When particle size is made to be nanoscale, properties such as melting point, fluorescence, electrical conductivity, magnetic permeability, and chemical reactivity change as a function of the size of the particle. As used herein, a "nanodevice" is a device formed from nanomaterials. Nanodevices and nanomaterials can interact with biological systems at fundamental, molecular levels with a high degree of specificity. By taking advantage of this unique molecular specificity, these nanotechnologies can stimulate, respond to and interact with target cells and tissues in controlled ways to induce desired physiological responses, while minimizing undesirable effects.

Nanowires have been shown to function as phototransistors with high sensitivity. Due to the small lateral dimensions (100's of nm to 10's of µm) and large surface-to-volume ratio of silicon (Si) nanowires, the large number of states at a Si surface can trap carriers at the surface equivalence to a gate bias, resulting in phototransistive behavior that leads to high sensitivity. This unique property of Si nanowires makes these devices attractive for photodetection from ultraviolet to the near infrared. Zhang, A., et al. ("Silicon Nanowire Detectors Showing Phototransistive Gain", *Applied Physics Letters,* 2008, Vol. 93, 121110-1-3) have shown that etched planar and vertical Si nanowires function effectively with gains exceeding 35,000 under low intensity UV illumination, demonstrating their potential for low light detection. The vertical Si nanowires in particular are effective at overcoming low physical fill factor (FF) limitations due to their strong waveguiding effects, which cause a large fraction of the photon energy to be funneled into the nanowires.

SUMMARY OF THE INVENTION

It is an advantage of the present invention to provide a retinal implant for at least partially restoring vision to patients suffering vision loss due to retinal disease.

It is another advantage of the invention to provide a nanoengineered retinal prosthesis with light sensing and stimulation elements that exhibit light sensitivity and spatial distribution comparable to that of rods and cones of the eye.

In one aspect of the invention, nanophotonic technology replaces the light sensing and signal transduction functions of damaged photoreceptors in the eye. In an exemplary embodiment, semiconductor vertical nanowires are fabricated using a nanoimprint lithography (NIL) technique for use as a light sensing component and for neuron stimulation in a retinal prosthetic device. Silicon (Si) nanowires provide the light sensing component of the implant, producing a photocurrent that is proportional to the intensity of light. The photocurrent produced can then be used to stimulate the neurons that would, in a healthy eye, be stimulated by the rods and cones.

A Si nanowire array provides an effective replacement for photoreceptors due to near single photon sensitivity as well as the ability to tailor the size and spatial distribution of the nanowire arrays to mimic the natural retina. These characteristics present the potential for fine control over the tissue interface and stimulation. In addition, providing a light-sensitive component to the retinal prosthesis, instead of relying on external cameras to capture images, makes use of the natural ability to track objects and reduces the amount of power required for the equipment that is worn by the patient.

In one aspect of the invention, a prosthetic retina for implantation in an eye having a retina that is defective is formed from an array of nanowires having a predetermined spatial distribution, density, size and shape implanted in close proximity to the retina; an electrical conductor disposed at a first end of all nanowires in the array of nanowires; a bias source in electrical communication with the electrical conductor for biasing the array; and a plurality of electrodes disposed on a second end of each of one nanowire or a bundle of nanowires in the array of nanowires, wherein each nanowire produces a photocurrent at a corresponding electrode in response to detection of light impinging on the array of nanowires, wherein the photocurrent stimulates one or more neurons adapted for visual perception. In one embodiment, each nanowire has a diameter ranging between 200 nm-5 µm and a height ranging between 1-50 µm. A spacing between nanowires in the array may be on the order of 2 nm or more. In a preferred embodiment, the predetermined spatial distribution mimics a distribution of rods and cones in a normal eye.

In another aspect of the invention, an implantable device is provided for detecting a triggering signal within tissue and generating an output signal therefrom. The device includes an array of nanowires having a predetermined spatial distribution, density, size and shape implanted in a location within the tissue within which the triggering signal is received; an electrical conductor disposed at a first end of all nanowires in the array of nanowires; a bias source in electrical communication with the electrical conductor for biasing the array; and a plurality of electrodes disposed on a second end of each of one nanowire or a bundle of nanowires in the array of nanowires, wherein each nanowire produces a current at a corresponding electrode in response to detection of the triggering signal, wherein the array of nanowires generates an output signal corresponding to the currents produced in response to the triggering signal. In one embodiment, the triggering signal may be light impinging on the tissue and the output signal may be a signal for stimulating one or more photoreceptor neurons. In another embodiment, a recording device comprising an amplifier and a memory device is provided so that the output signal is communicated to the recording device for amplification and storage in the memory device. The implantable device may further include an electrically-reactive membrane having a plurality of openable cells for retaining a neurotransmitter, wherein the electrically-reactive membrane is in electrical contact with the plurality of electrodes, and wherein the output signal activates the electrically-reactive membrane to release at least a portion of the neurotransmitter in response to detection of light.

In still another aspect of the invention, an implantable device for detecting an electrical potential within a tissue and generating an output therefrom is provided. The device includes an array of nanowires; an electrical conductor disposed at a first end of all nanowires in the array of nanowires; a bias source in electrical communication with the electrical conductor for biasing the array; a plurality of electrodes disposed on a second end of each individual nanowire or each bundle of nanowires in the array of nanowires, wherein one or more pairs of individual nanowires or bundles of nanowires, when implanted within tissue, detects an intracellular or extracellular action potential within the tissue and generates an output signal at the electrical conductor; and a recording device comprising an amplifier connected to the electrical conductor for receiving and storing a signal corresponding to an amplified intracellular or extracellular action potential.

In yet another aspect of the invention, a method is provided for forming a prosthetic retina, where the method includes the steps of forming an semiconductor layer on a substrate; coating an upper surface of the semiconductor layer with a photoresist; imprinting a pattern in the photoresist with a mold adapted to define a plurality of features with a predetermined spatial distribution, density, size and shape; anisotropically etching the photoresist to expose areas of the semiconductor layer surrounding the plurality of features; coating the photoresist and exposed areas of the semiconductor layer with a conductive coating; removing the photoresist to define conductive areas corresponding to the plurality of features and to selectively lift the conductive coating from areas of the semiconductor layer surrounding the conductive areas; anisotropically etching the semiconductor layer surrounding the conductive areas to define an array of vertical nanowires separated by channels; filling the channels with a biocompatible insulating material, wherein the insulating material is adapted to permit nutrients to be conducted therethrough; forming electrical contacts on an upper end of each nanowire of the array of vertical nanowires, wherein the electrical contacts are adapted to stimulate neurons for visual perception; and removing the substrate to expose a lower end of each nanowire of the array of vertical nanowires. In an additional step, the array of vertical nanowires may be attached to a flexible substrate.

DETAILED DESCRIPTION

According to the present invention, a novel retinal prosthesis is provided in which the artificial photosensors incorporated in the prosthesis have essentially identical, or similar, density, light sensitivity, dynamic range in response to light illumination and response kinetics to the rods and cone photoreceptors they are replacing in the diseased eye.

In an embodiment of the invention, silicon nanowires (NW) serve as the light sensing component of the inventive implant. When light impinges on the implant, a photocurrent that is proportional to the intensity of light is produced. This photocurrent may be used to stimulate the neurons typically stimulated by the rods and cones. The high intrinsic gain of the NW array in particular is very useful for prosthesis applications because it allows for high pixel resolution which cannot be achieved with traditional silicon devices because in traditional devices most of the pixel space is taken over by amplification circuitry, reducing the photosensitive area.

Functional organization of the photoreceptors (PRs) in the retina provides a challenge for prosthetic intervention aimed at replacing the retina's ability to detect light with high visual acuity. An example of this specialized organization of the PR is the fovea, which owes its high visual acuity to the ratio of ganglion cells to PRs, which can be as high as one to one. The density of cones in the human retina range between 90,000-300,000 cones/mm$^2$, while rods can reach 179,000 rods/mm$^2$, decreasing by around 10-15% across the retina. In addition to their distribution, rods and cones have a range of height between 40-50 μm long while their diameter varies between 0.50 to 4.0 μm. The size of the PRs and their density also provide a specialization since it governs photon interaction areas.

The inventive technology provides an ideal replacement for photoreceptors due to near single photon sensitivity, and the ability to tailor the size and spatial distribution of the nanowire arrays. These characteristics present the potential for fine control over the tissue interface and stimulation. In addition, providing a light-sensitive component to the retinal prosthesis, instead of relying on external cameras to capture images makes use of the natural ability to track objects and reduces the amount of power consumption by the equipment worn by the patient.

Figure 5A:
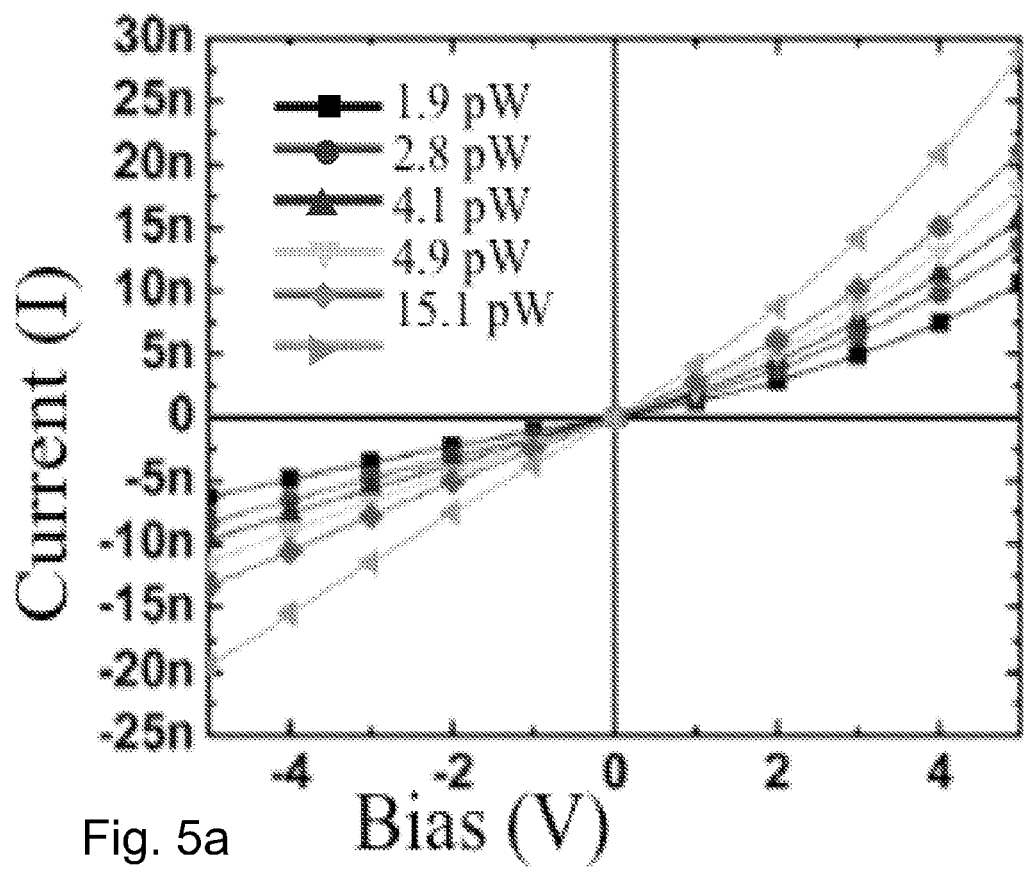
FIG. 5a is a plot of current versus voltage of a single nanowire array under light stimulation.
Figure 5B:
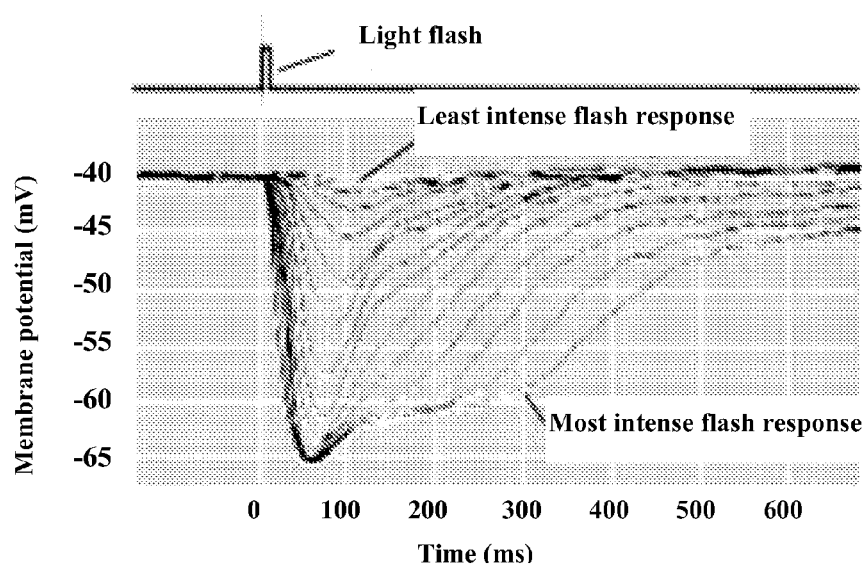
FIG. 5b is a plot of membrane potential changes with time in cone cells in response to light.

Both rods and cones are capable of phototransduction. PRs respond to light stimulation by changing their membrane potential to a more hyperpolarized state, which alters release of neurotransmitters. In parallel, the nanowires are capable of phototransduction and are well documented as high sensitivity photodetectors. When visible light illuminates the nanowires, electron-hole pairs are generated. The electrons are instantly driven to the surface, leaving the holes in the center of nanowires. FIG. 5a shows the current versus voltage curve of a single NW array under light stimulation. The surface has an accumulation of positive charge due to Fermi pinning. As a result, the originally insulated nanowires become electrically conducted for the duration before the holes in the nanowires are finally trapped to the surface again, which might take <1 μs to 1 ms depending on the intensity of light. This is superior to the response time of 70-120 ms of rods and cones (depending on background illumination). For comparison, FIG. 5b shows the changes in membrane potential in cone cells in response to light.

Figure 6A:
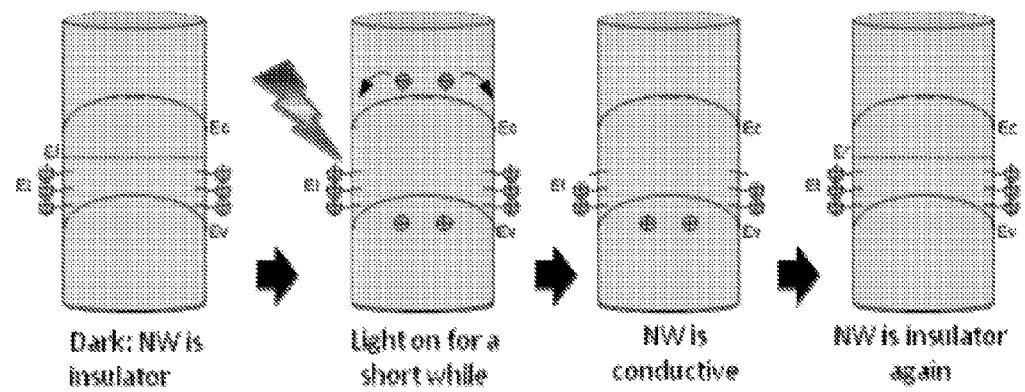
FIG. 6a provides a diagrammatic energy band diagram of silicon nanowires.

Without illumination, the nanowires behave as insulators because all mobile charges, i.e., holes, in the nanowires are completely depleted. FIG. 6a provides an energy band diagram of silicon nanowires for the preferred embodiment of the NW structure (p$^+$/p$^-$/p$^+$). The holes in the p$^-$ region are all depleted from the center and trapped in the surface states. The trapped charge at the surface creates a radial potential profile as shown. When a photon is absorbed by the nanowire to excite an electron-hole pair, the electron is instantly attracted to the surface and recombined with the trapped hole due to the radial potential, leaving the hole in the center of the nanowire to form a conductive channel. As soon as the nanowire becomes a conductive channel due to the presence of a hole that is free to move, current flows continuously from the anode to the cathode. This potential acts to stimulate the neurons in the proximity of the wires.

There are three types of reactions through which neural stimulation can occur:

1) Capacitive, in which there is no electron transfer, but instead electrostatic electrolyte dipole orientation occurs. This approach requires the charge to be stored across a high-dielectric-constant oxide;

2) Faradic, which requires transfer of an electron across the interface between NW tips and the tissue, facilitated by an oxidation reaction or reduction reaction; and 3) Pseudocapacitive, which includes electron transfer, so it is partly faradic, but an electrode coating can be used to store and inject charge. These electrode coating must be able to undergo reversible reduction-oxidation (multivalent, e.g., ethylenedioxythiophene, iridium oxide or any mixed conductor that can facilitate ion and electron transfer). Studies have shown that 3D structures such as the NW can provide more charge for stimulation.

Typically, the current waveform for neural stimulation is a monophasic or biphasic current pulse. The amount of charge needed to stimulate the retina is around 1 μC (Coulomb), delivered over 5 msec, with a charge density of 1 mC/cm$^2$. Current used for stimulation=200 μA, with a maximum frequency=100 Hz. The nanowires produce a photocurrent in response to light stimulation, which can be modulated by the applied bias.

The inventive nanowire platform enables creation of an interface that is effectively a direct material-cell membrane biophysical interaction. The interface between the nanoarrays and neurons is fundamentally biophysically and molecularly unique, involving molecular interactions that result in greatly enhanced abilities to stimulate and record using minimal input energy, e.g., currents, when stimulating. This nanoscale interface also makes it possible to record with excellent signal-to-noise ratios, requiring minimal amplification due to the intimate molecular interface between the nanowires and the neuronal cell membrane. These advantages are a direct result of the nanoscale engineering of the device and material.

Figure 6B:
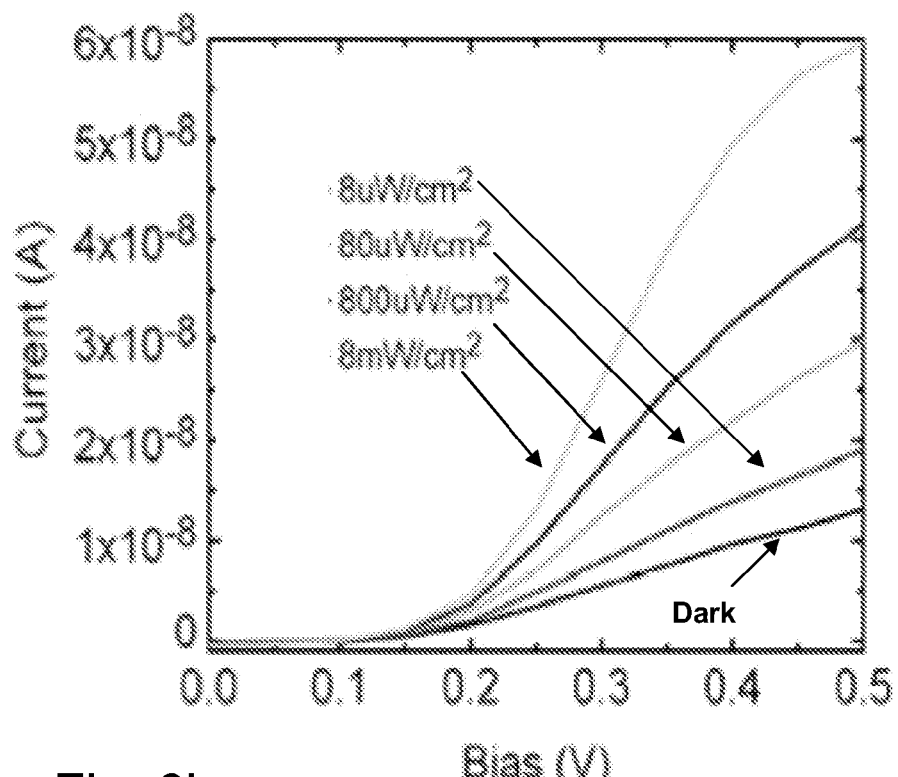
FIG. 6b is a plot of the I-V characteristics of silicon nanowire detectors at different light intensities.
Figure 6C:
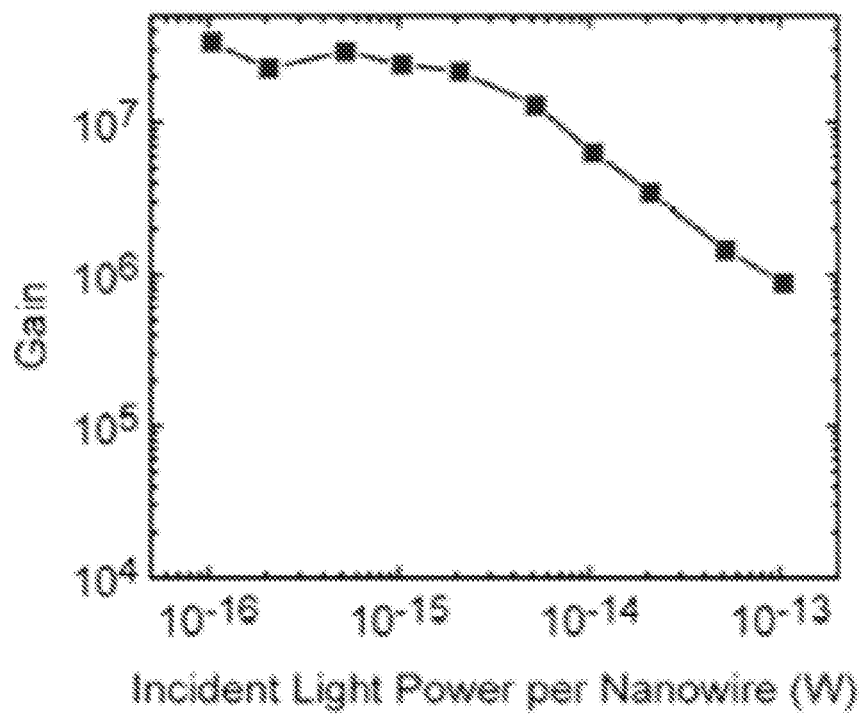
FIG. 6c is a plot of gain as a function of incident light intensity at each nanowire.

Looking at the photoresponse of the nanowires, it can be compared to changes in the membrane potential of cone cells, as shown in FIGS. 6b and 6c. FIG. 6b is a plot of the I-V characteristics the silicon nanowire detectors at different light intensities, showing the increase in current output of the nanowires as light intensity increases. Photocurrent increases by less than 10 times as the light intensity increases by 1,000 times, demonstrating the characteristics of optical adaptation. FIG. 6c is a plot of gain as a function of incident light intensity to each nanowire, showing that, similar to cones, the photoresponse of a silicon nanowire detector saturates as the light intensity increases. This is the intrinsic gain, without taking into account the external light coupling efficiency, which is between 5-10%. It should be noted that 8 $\mu W/cm^2$ in FIG. 6b corresponds to $1\times10^{-14}$ W in FIG. 6c because FIG. 6b shows a total response of ten nanowires. Thus, changes in light intensity induce an increase in photocurrent, similar to increase in membrane potential of the cone cells in response to increase intensity of light.

The rods and cones can operate on an extremely large range of illumination; the lowest is 10-100 lux. This is due to light responsive ion channels and also to neural interactions between horizontal cells and photoreceptor terminals contribute to the reduction of amplification with increasing light intensity. The nanowires can be made to mimic this control via feedback control that governs the level of bias voltage. Looking at FIGS. 5b and 5c, the photocurrent response can be changed by changing the voltage applied to the nanowires, providing control over the output. In addition, the nanowires can respond to light as low as 0.1 fW ($10^{-16}$ W), corresponding to illumination of (6-10 lux).

Figure 7:
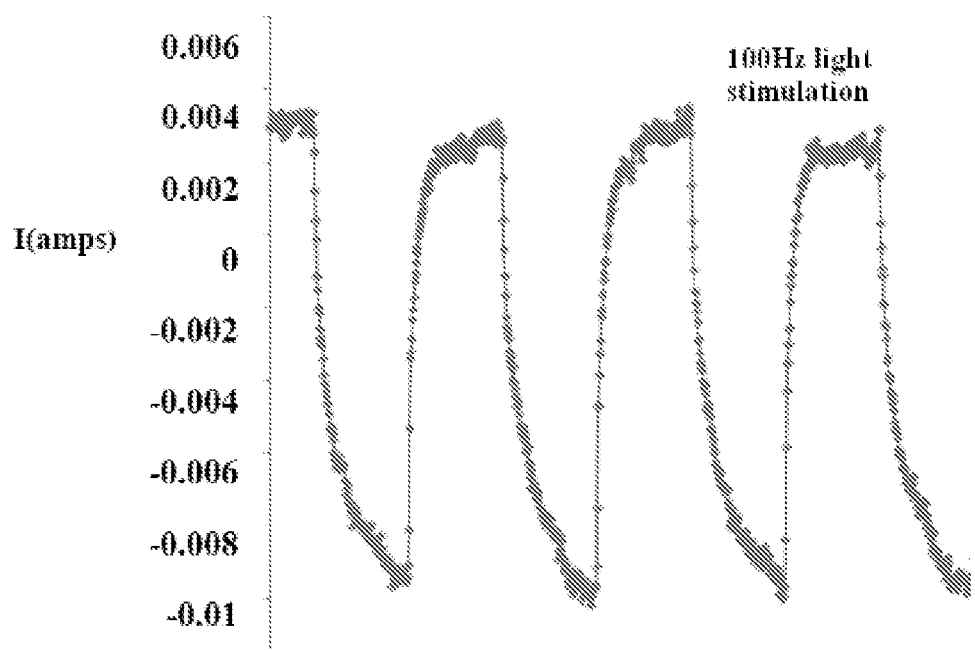
FIG. 7 shows the current response of a 100 nanowire array to light stimulation frequency of 100 Hz, light intensity 100 μW mm$^{-2}$.

Photoreceptors stimulate neural tissue via the release of neurotransmitters. Neurons can also be excited via current stimulation by driving a current through neural tissue. Artificially, depolarizing the cell membrane can be done by flowing ionic current between two electrodes. One of these two electrodes must be near the tissue. In the case of the present invention, this electrode is the nanowires. The photocurrent waveform can be altered via control circuits, as described below. Referring to FIG. 7, the waveform includes cathodic (reduction of the stimulator, NW) and anodic (oxidation of the stimulator, NW) phases, which are designated in the figure by $t_c$ and $t_a$, respectively. The current delivered by the stimulating electrodes must be balanced with no accumulation of charge and avoid damage to the tissue. FIG. 7, which shows the current response of a 100 NW array to light stimulation frequency of 100 Hz at a light intensity of 100 $\mu W$ $mm^{-2}$, provides examples of three balanced waveform types that can comply with such requirements. Basically, the electron flow in the NW must be converted to an ionic flow in the tissue by a reaction at the metal tips.

Figure 8:
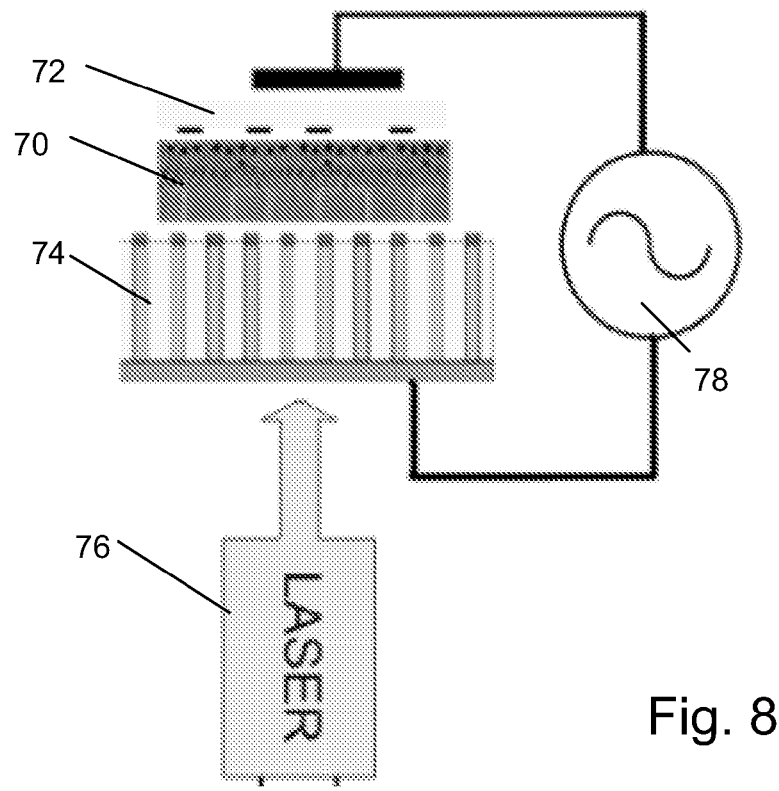
FIG. 8 is a diagrammatic view of an exemplary set-up for neurostimulation.
Figure 9:
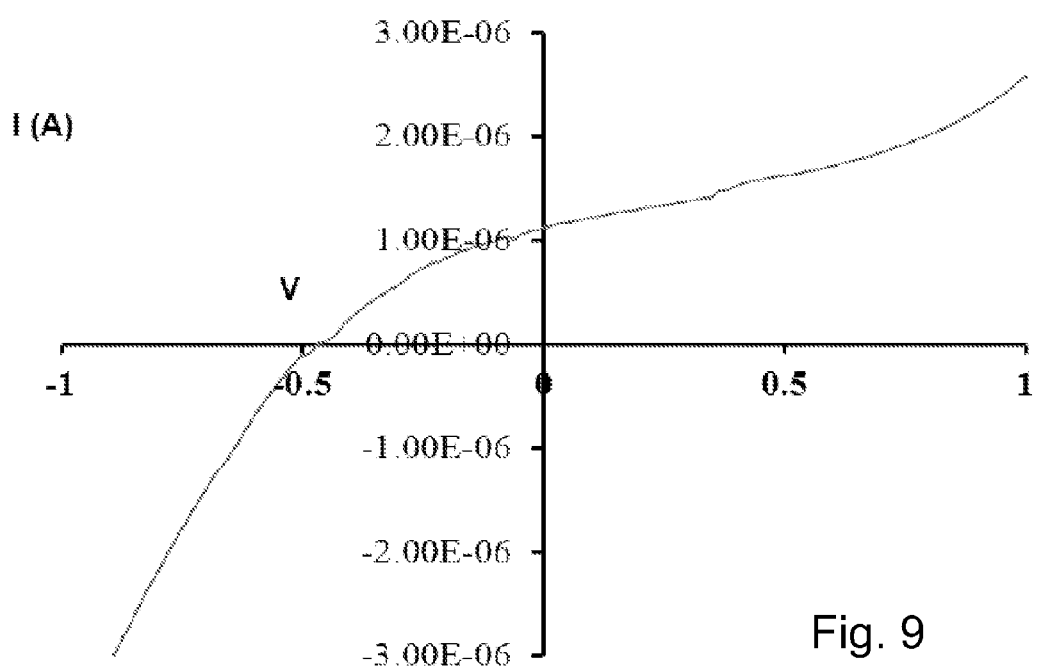
FIG. 9 is a IV curve of a 1 mm$^2$ nanowire array under light stimulation of 1 μW mm$^{-2}$.

Nanowires can be used to produce a photocurrent to stimulate neurons to fire action potential in both monopolar and bipolar stimulation setups. If done in the retina, the stimulation will lead to visual percepts whether the stimulation is at the epiretina or subretina side. FIG. 8 illustrates an exemplary set-up for neurostimulation, where the retina 70 is placed in contact with a transparent (microelectrode array) 72 to record RG (retinographic) activity. The photocurrent produced by the nanowire array 74 in response to illumination by laser 76 can be used to inject current into the retina when placed near the tissue. Results in FIG. 9 show that a nanowire platform such as that of FIG. 8 is capable of producing the current levels and waveforms necessary for neural stimulation. The IV curve in FIG. 5a shows nanowire response in setup similar to that of FIG. 8, where the ground is a distance away from the array 74 and the bias 78 is applied across the neural recording solution. Charles LeRoy was the first to show in 1755 that current stimulation of the retina can produce visual percepts in blind patients.

Figure 10A:
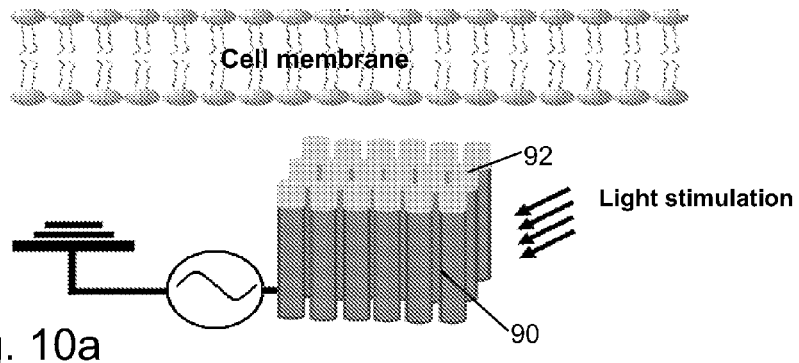
FIG. 10a is a first exemplary embodiment of a stimulation set-up using the inventive nanowire platform.
Figure 10B:
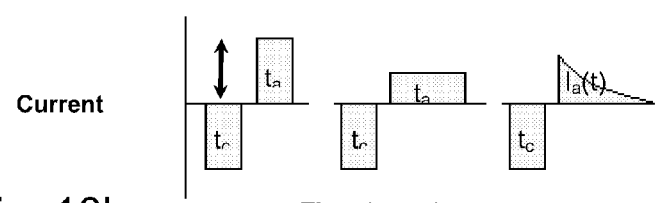
FIG. 10b shows the proposed current waveforms used to stimulate the array.

FIG. 10a is a diagram of an exemplary embodiment of an extracellular stimulation arrangement using the inventive nanowire platform with Si nanowires 90 and conductive metal (or metal oxide) 92. The number of nanowires per bundle is dependent on the current output of the nanowires and will range from 1 nanowire to 1000 nanowires. FIG. 10b provides an example of current waveforms that can be used to stimulate $t_a$ and $t_c$, which range between 0.1 msec to 10 msec.

Figure 11:
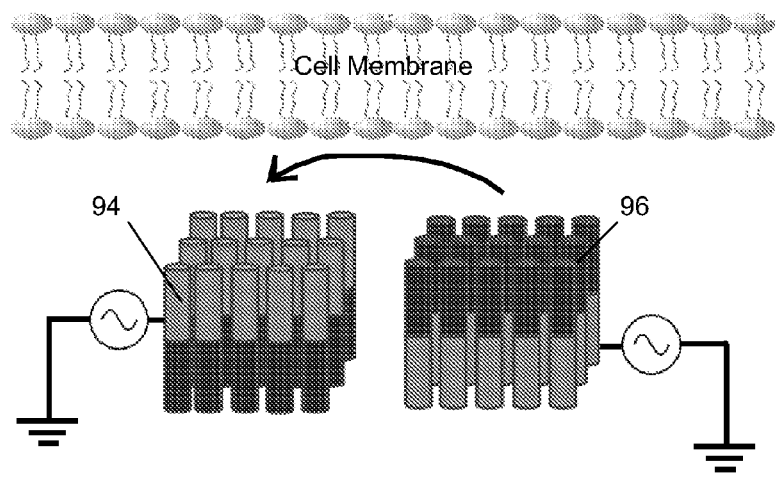
FIG. 11 is a second exemplary embodiment of a stimulation set-up using the inventive nanowire platform.

FIG. 11 provides an alternative embodiment of an extracellular stimulation arrangement according to the invention with two PN junction nanowire arrays 94, 96 in a bipolar stimulation setup. The arrow indicates the direction of the current.

In addition to extracellular set-ups, the inventive NW platform can be applied to applications of intracellular stimulation. Excitable cells such neurons and heart cells can be depolarized by the extracellular or intracellular flow of ionic current. For intracellular stimulation, the nanowires can be engulfed inside the cell.

Nanotopography has been shown to improve tissue integration of prosthetic devices and even accelerate recovery from injury. The nanowire platform according to the present invention has an inherit nanotopography that is able to interface directly with the ganglion cells in a setup similar to that illustrated in FIG. 8. Recent work has shown that using nanotopography at the site of stimulation reduces the amount of current required to stimulate neural tissue, thus allowing power consumption to be minimized while simultaneously reducing the occurrence of tissue damage caused by the stimulation.

In one embodiment of the invention, a silicon (Si) nanowire array is formed using a nanoimprint lithography (NIL) technique, which can be used as a light sensing component and neuron stimulator in a retinal prosthesis device. The nanoimprint lithography is described in Kim, H., et al., "Fabrication of Vertical Silicon Nanowire Photodetector Arrays using Nanoimprint Lithography", *Proceedings of SPIE*, 2010, pp. 7591-7595, which is incorporated herein by reference.

Figure 1:
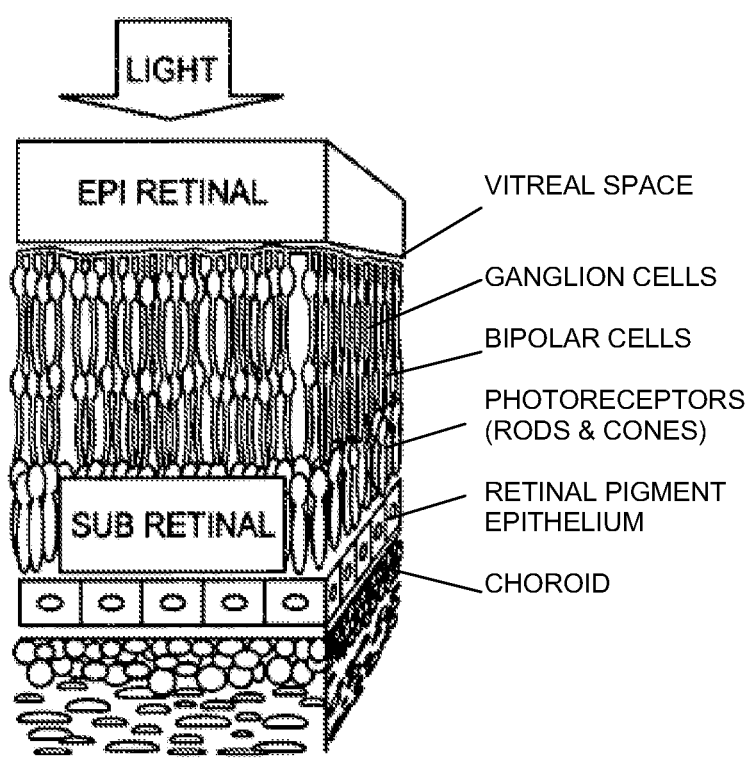
FIG. 1 is a section of a retina showing the possible placement sites of a retina prosthesis.
Figure 2A:
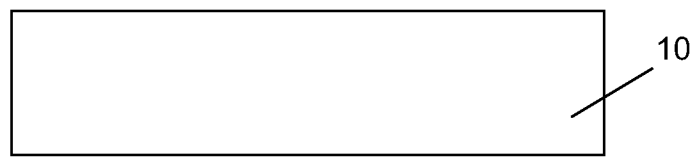
FIGS. 2a-2f diagrammatically illustrate the key steps in an exemplary process flow for forming of vertical Si nanowires starting with p+/p−/p+ silicon.
Figure 2B:
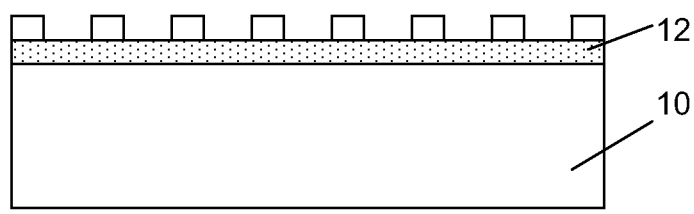
Figure 2C:
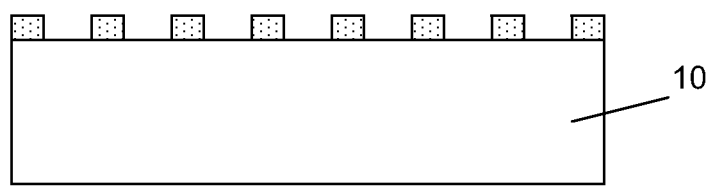
Figure 2D:
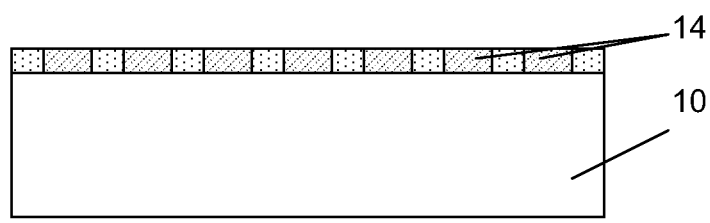
Figure 2E:
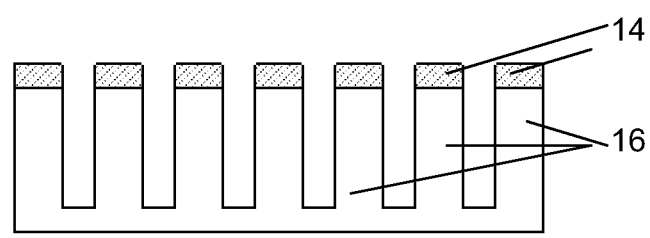
Figure 2F:
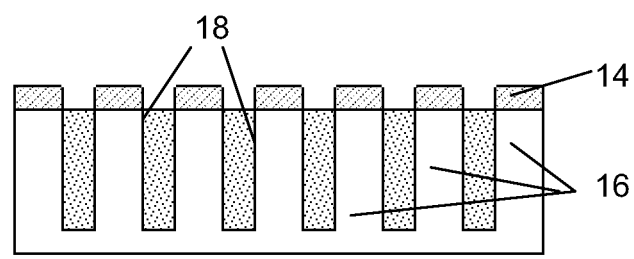
Figure 3:
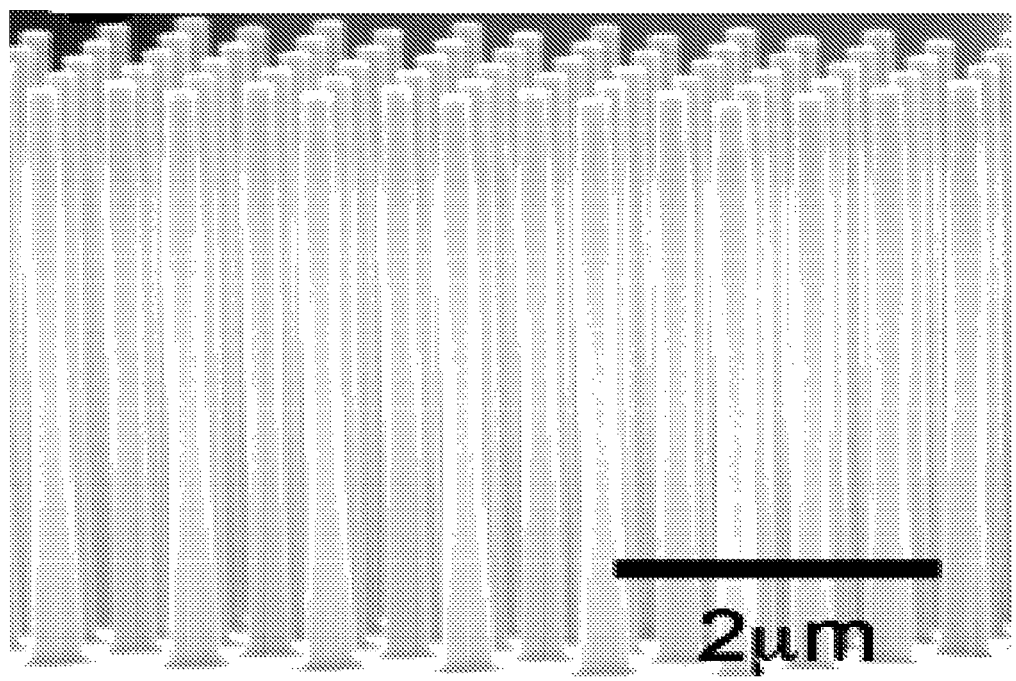
FIG. 3 is a photomicrograph of silicon nanowires formed using the process flow of FIGS. 2a-2f.

Nanoimprint lithography (NIL) involves physically pressing a mold, which has a nano-sized pattern, onto a photoresist-coated substrate. Generally, the NIL process consists of three steps: preparing a master mold, making a quartz working mold, and preparing the sample. Referring to FIGS. 2a-2f, the process for fabricating vertical silicon nanowires starts with a $p^+$ silicon <100> substrate with a lightly p-doped epitaxial layer covered by a heavily p-doped layer to form a $p^+/p^-/p^+$ Epi structure (FIG. 2a). Photoresist is coated onto the epi structure 10 and is imprinted by pressing a surfactant-coated quartz working mold into the photoresist 12 (FIG. 2b) to create nano-islands of photoresist and expose the Si surface in the imprinted areas. Preferably, the photoresist has a two-layer structure with an under-layer and a UV-layer. The imprinted photoresist is cured using standard procedures according to manufacturer's specifications, followed by a reactive ion etch (RIE) process (two step RIE process if the preferred bi-layer PR is used) to expose the silicon surface in the imprinted areas (FIG. 2c). A ~70-80 nm layer of nickel 14 is deposited by evaporation and the photoresist nano-islands are lifted off to form an etch mask and to make ohmic contact with the upper $p^+$ region (FIG. 2d). This forms an array of Ni dots 14 on the Si surface. RIE is used to etch the exposed Si between the Ni dots, defining the nanowires 16 in the Epi silicon (FIG. 2e), followed by annealing the Ni for hour at 650° C. The area between the nanowires 16 is filled with an insulating material 18 by spin coating the surface, baking for 5 minutes at 80° C., and using RIE to etch back the coating to expose the Ni tips (FIG. 2f). In some applications, it may be desirable to etch the coating back an additional amount to expose anywhere from 0.1%-50% of the lengths of the nanowires. In an exemplary embodiment, the insulating material 18 is polydimethylsiloxane (PDMS), but other materials known in the art may be used, including PARYLENE™ (poly(p-xylylene) polymers (all types, such as HT and C)), polyimide (all types), and poly(methylglutarimide (PMGI)). FIG. 3 is a scanning electron microscope (SEM) image of nanowires formed by the NIL process.

Figure 4A:
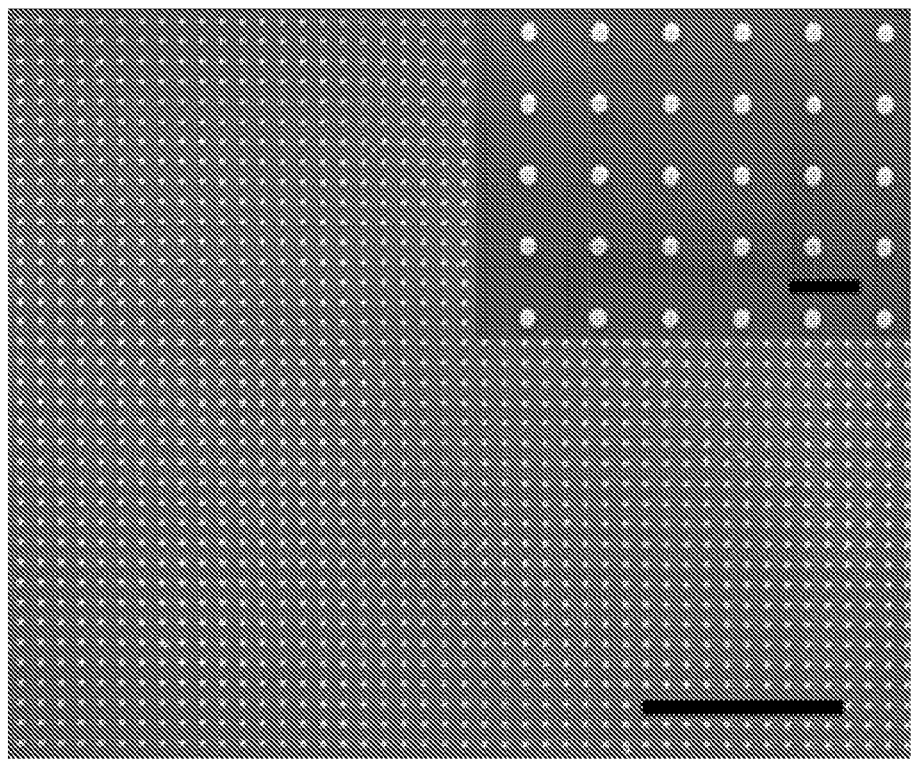
FIGS. 4a and 4b are top and side view photomicrographs, respectively, of nanowire arrays.
Figure 4B:
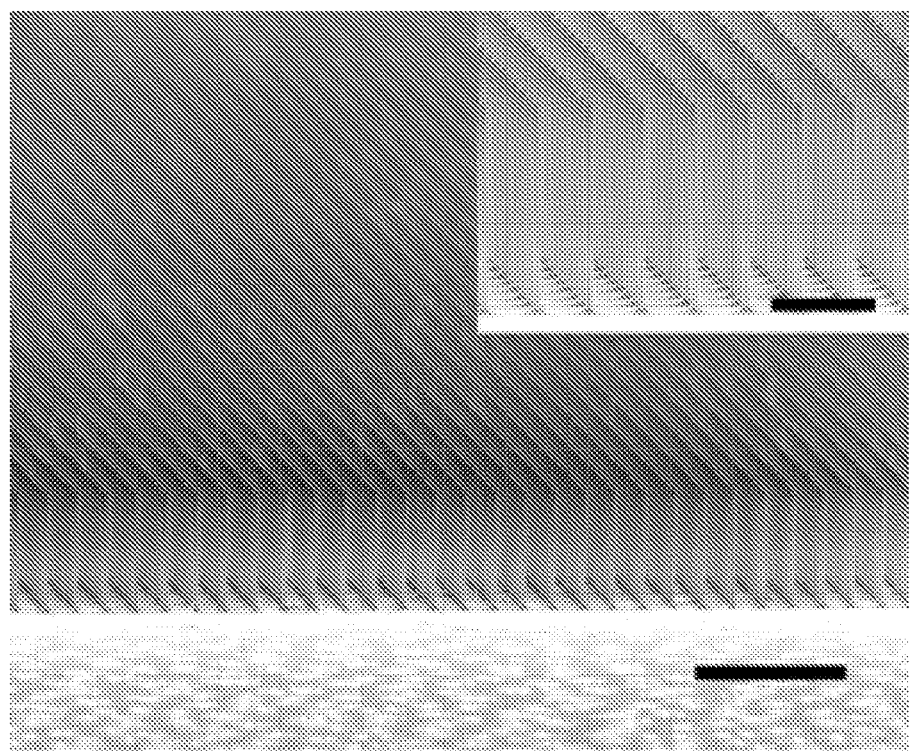

The advantage of using nanoimprinting to manufacture the nanowire array provides control over spatial distribution and form factor. This allows for control over spacing between the nanowires down to 2 nm, diameters ranging between 10 m-5 μm, and lengths ranging between 1-50 μm. This provides the ability to tailor the nanowires to fit the distribution of the PRs they are replacing, if appropriate. Virtually any distribution pattern can be formed using the NIL process, adapted for the requirements of the particular application. FIGS. 4a and 4b, which are SEM images of a NW array, provide one example of NW distribution. (The bars in the image represent 1 μm.) These properties make the nanowires an excellent replacement for the photoreceptors. In addition, the nanotopography resulting from the wire structures will aid in tissue integration and neuronal rewiring.

In addition to top-down processes such as the process illustrated in FIGS. 2a-2f, bottom-up fabrication processes may be used to create appropriate NW arrays for use in the inventive implant. For example, conventional photodetector concepts and architectures (semiconductor p-n or p-i-n photodiodes) can also be made into nanowire structures. These types of nanowires are most commonly manufactured via chemical vapor deposition (CVD) growth. One example of a process form forming NW arrays is described by Wei, et al. ("Direct Heteroepitaxy of Vertical InAs Nanowires on Si Substrates for Broad Band Photovoltaics and Photodetection" *Nano Letters*, 2009, 9 (8), pp 2926-2934). Briefly, vertical InAs nanowire arrays were grown in a close-coupled showerhead MOCVD (metal-organic CVD) system. Prime quality p-type Si <111> wafers were diced and cleaned with solvents in an ultrasonic bath. The substrates were etched using diluted buffered oxide etch (BOE 6:1) for 30 seconds to remove the native oxide, rinsed in deionized water for about 15 second, and dried with nitrogen. The substrates were loaded into the MOCVD chamber where growth was effected using arsine ($AsH_3$) and trimethylindium (TMI) precursors in a hydrogen carrier gas with a total flow rate of 20 L/min at 100 Torr chamber pressure. The substrates were heated up to the growth temperature ranging from 535 to 550° C., and after a short stabilization time, the growth was initiated by simultaneous introduction of arsine and TMI to the reactor chamber with molar fraction of $2\times10^{-4}$ and $2\times10^{-6}$, respectively. The growth was terminated by interrupting the TMI flow, while the arsine flow was retained until the reactor was cooled down to 250° C. to prevent decomposition of the InAs nanowires. Packaging of the InAs nanowires photodetectors is similar to the NIL-formed nanowires, where an insulator, such as described above is coated on the structures and etched away to expose the tips. A metal conductor such as ITO (indium tin oxide), or other appropriate metal or metal alloy, may be used to cover the tips to ensure good electrical contact. Additional details are provided by Dayeh, et al. in *Nano Today*, "Advances in the synthesis of InAs and GaAs nanowires for electronic applications", (2009) 4, 347-358.

Group VI (Si, Ge) and compound (III-V, II-VI, SCSSC and hybrid) semiconductor nanowires that may be used to form the inventive nanowire platform can be synthesized using a variety of techniques including organo-metallic vapor phase epitaxy (OMVPE), chemical and molecular beam epitaxy, CVD, laser ablation and low-temperature solution techniques as well as E-beam lithography. Suitable materials for use in forming the inventive nanowire array devices include, but are not limited to Si, Ge, GaN, GaAs, InAs, InP, ZnO/ZnSe, ZnO, $TiO_2$, CdSe, CdS, CdSe, CdTe, $ZnO/TiO_2$, and ZnO/CdSc.

Vertically-aligned arrays of Si nanowires may also be formed on a <111> Si substrate by gold (Au)-catalyzed selective vapor-liquid-solid (VLS) growth. The NWs may be synthesized in a vacuum chamber using disilane ($Si_2H_6$)-phosphine ($PH_3$) gas as the growth sources and gold as the growth catalyst. The Si gas source for n-type Si probes with a resistivity on the order of $10^{-2}$ Ω-cm (impurity concentration of $10^{18}$ cm$^{-3}$) can be obtained using a mixture gas of 1% phosphine diluted in 99% hydrogen with 100% disilane. VLS growth was performed at a gas pressure of 0.6 Pa and a temperature of 700° C., resulting in a growth rate of 1 μm/min. Additional details of the process can be found in "Heterogeneous Integration of Vapor-liquid-solid Grown Silicon Microprobe Arrays/(111) and MOSFETS/(100) using a Silicon on Insulator Substrate, *Micro Electro Mechanical Systems (MEMS)*, 2010 *IEEE 23rd International Conference on*, Jan. 24-28, 2010, pp 372-375.

Patterning of the CVD-grown nanowires to select predetermined nanowire dimensions and spatial distribution patterns for the desired application may be achieved by photolithography in conjunction with reactive ion etch (RIE) or E-beam lithography. The key to the inventive nanowire platform for implants is the ability to precisely control dimensions and spatial distribution on a nanoscale. This level of precision may be achieved through top-down or bottom-up formation of the nanowire arrays.

To test tissue integration, rat cortical cultures were grown around the nanowire array. Tissue growth and integrated was observed on the nanowires. Initial cytotoxicity tests indicate that the nanowire chips have no toxic effect on cortical cultures.

In one embodiment of the invention, the nanowires can be fabricated on a substrate such as PARYLENE™, instead of Si, to take advantage of its superior biocompatibility and long term stability. PDMS (polydimethylsiloxane), which has similar properties, may also be used as a substrate. PDMS is an optically transparent, non-toxic elastomer with high permeability to allow provision of nutrients. Other polymers with similar properties may be also be used. Selection of appropriate materials will be readily apparent to those of skill in the art.

An important step in the fabrication of NWs is formation of the contact electrodes to each nanowire. This electrode (typically consisting of Ti/Au, although other metals may be used) should connect all nanowires, which are about 1 μm apart, without blocking channels for nutrients needed to maintain the health of the retina. FIGS. 11a-11e illustrate an exemplary process flow to remove the nanoimprinted silicon nanowire arrays from its native silicon substrate to a flexible substrate formed from a polymer such as PDMS, PARYLENE™ or other materials with similar properties.

Figure 12A:
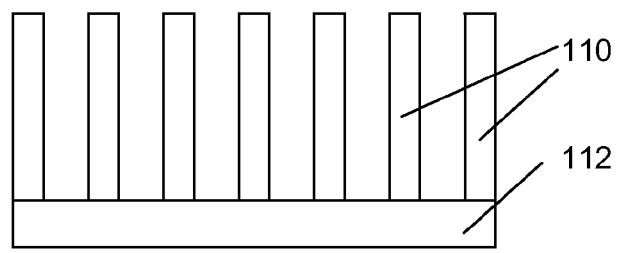
FIGS. 12a-12e diagrammatically illustrate the key steps in an exemplary process flow for forming a nanowire artificial photoreceptor according to the present invention.
Figure 12B:
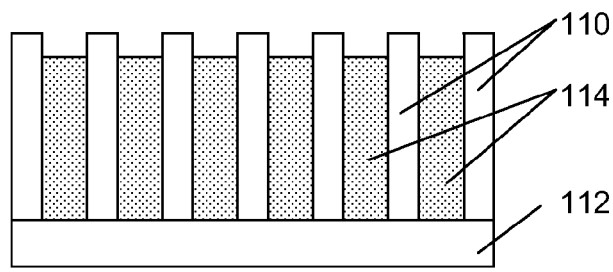
Figure 12C:
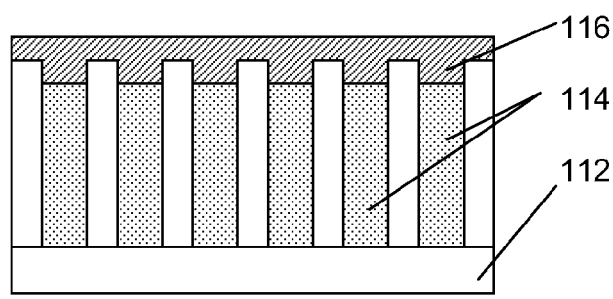
Figure 12D:
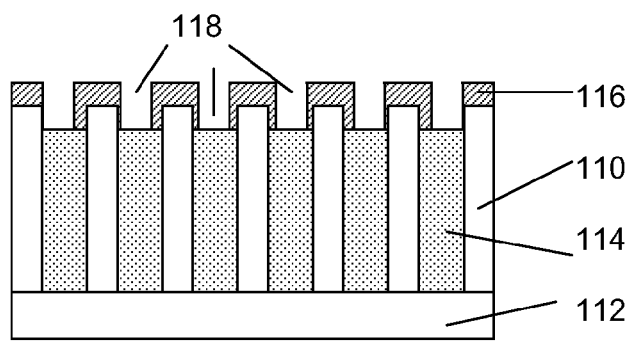
Figure 12E:
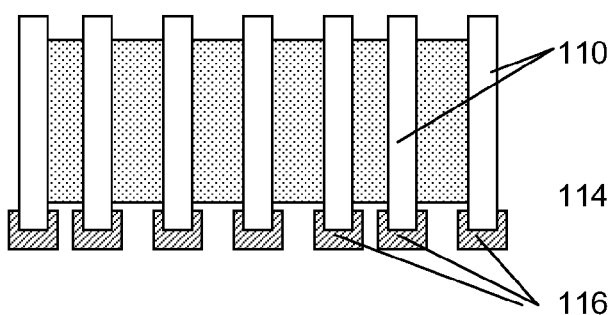

After formation of nanoimprinted Si nanowires 110 on an SOI (silicon-on-insulator) wafer 112 (FIG. 12a), a layer of PDMS membrane 114 is spin-coated onto the substrate (FIG. 12b). After partial removal of the layer to expose the tips of nanowires, a layer of Ti/Au 116 is deposited to form contacts with the nanowires (FIG. 12c). UV lithography is performed to open up holes 118 in the spaces between the nanowires (FIG. 12d) to provide nutrient supply channels to the retina. The exact size and position of these holes on the Ti/Au metal layer is not critical, as long as they are located in the spaces between the wires. The final step (FIG. 12e) is to release the wires from the SOI substrate 112 by removing the buried oxide layer. (The NW array is shown inverted in FIG. 12e.) The released structure can be placed onto a PDMS handle wafer to facilitate handling and material transfer.

Figure 13B:
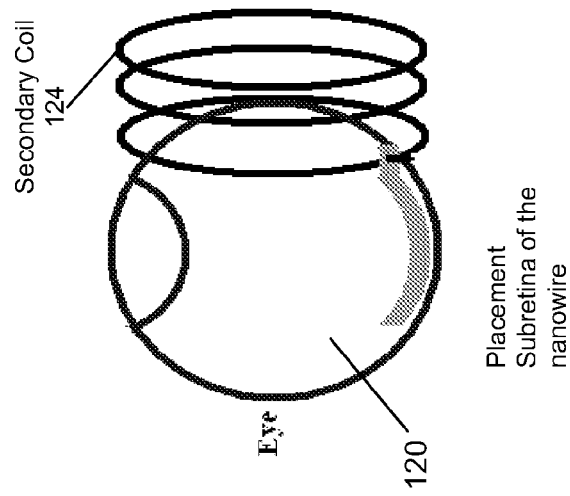
FIG. 13 is a diagrammatic view of a wireless circuit for a prosthetic implant according to the invention.
Figure 13A:
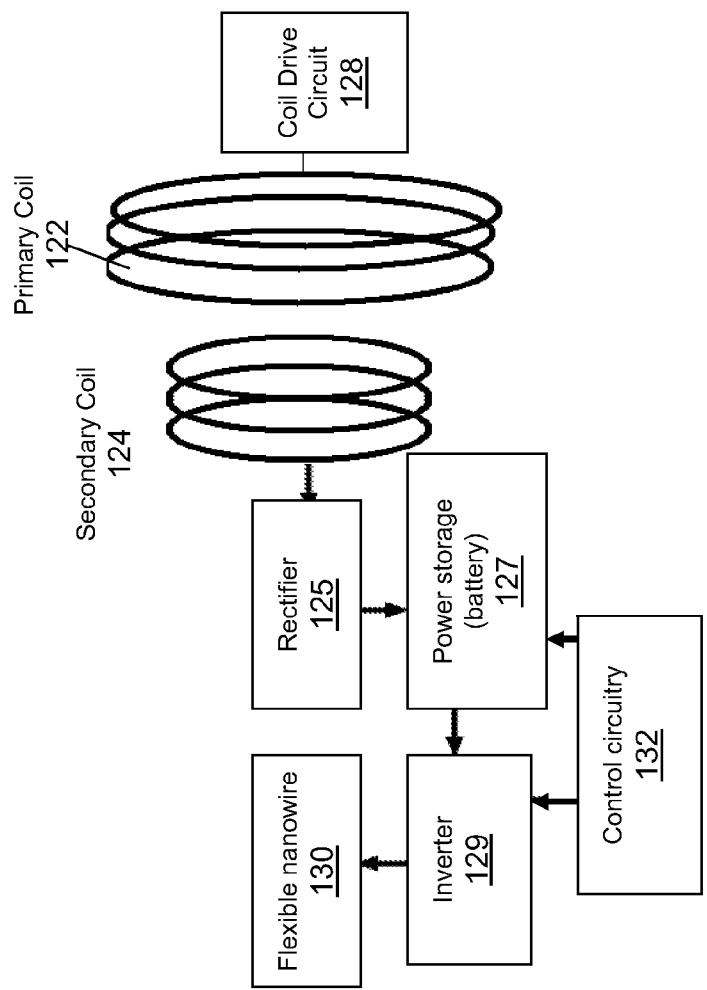

One approach for powering the prosthetic devices uses coupled coil transmission—this approach has been adopted by groups involved in the retinal prosthetics. Referring to FIG. 13a, the coil transmission assembly can include an AC magnetic field generated by a primary coil 122 on the outside of the eye 120, mounted, along with a coil drive circuit 128, on a pair of glasses that can be worn by the patient. Placement of the secondary coil 124 can be at the temporal side of the eye 120, as shown in FIG. 13b, to simplify transmission. This allows the coil and electronics to be attached to the sclera on the outside of the eye, while the electrodes of the nanowire array extend through a flap in the sclera to the subretinal space. Alternatively, the coil 124 could be placed against the retina, which would be most convenient since the coil, electronics and nanowire array could be implanted as one package. However, the fragility of the retina precludes placement of a thick or heavy implant, thus limiting the possible power that could be delivered. Placing the coil in the anterior chamber would allow more power to be delivered but is surgically difficult. Another alternative is to place the coil on the outside surface of the eye under the conjunctiva on the front of the eye. This location, or the location on the temporal side of the eye, allows the greatest amount of power to be delivered.

The design of secondary coil 124 will be limited by the maximum space around the eye and the heating due to the magnetic field (ANSI limit for field induced power in a tissue is 178 µW). The wireless circuit shown in FIG. 13a includes a rectifier 125 to convert the AC field induced by the primary coil 122 to DC for storage by battery 127. This is a typical design for inductive power delivery. However, because the nanowires 130 require AC bias to produce the biphasic currents needed for neural stimulation, an inverter 129 is included to convert the DC back to AC. Control circuitry 132 is connected to battery 127 and inverter 129 for controlling operation of the nanowire array 130. This design, although expected to be robust, would consume excessive of power.

In an alternative embodiment, the rectifier and inverter are eliminated, and the AC induced field is used to directly power the nanowires. In this embodiment, it may be advantageous to change the site or size of secondary coil to improve alignment with the primary coil.

Figure 14:
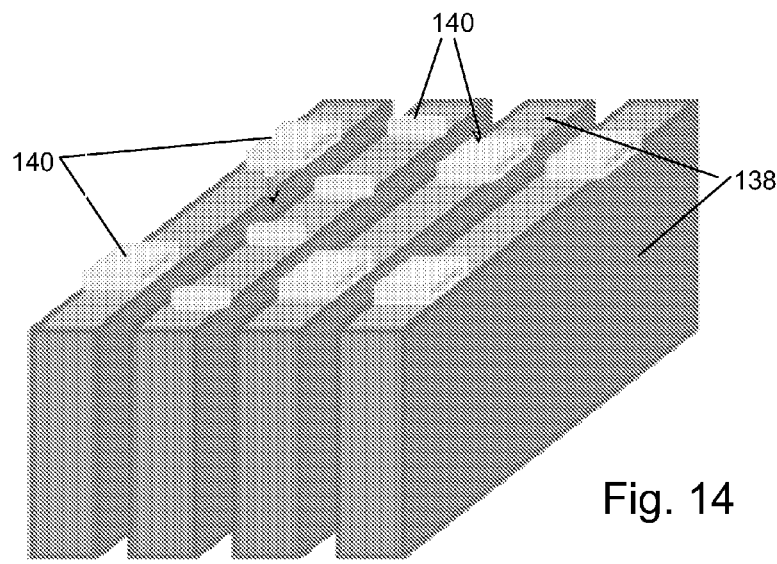
FIG. 14 is a diagrammatic perspective view of nanowire ridges for line stimulation.

A nanowire-based device constructed according to the present invention will carry a scalable modality capable of dual function of light detection and neural stimulation with tunable performance FIG. 14 is a diagram of nanowire ridges 138 pattered over a silicon substrate. In human and primate retinas, a small central area of the macular region of the retina called the 'fovea' is specialized for high resolution vision and sensitivity to fine details. The center of the fovea, the foveola, has a high concentration of very compact cones and virtually no rods. The fovea plays a key role in visually guided behavior. It has been shown that line-shaped stimulation electrodes can lead to selective activation of local ganglion cells, avoiding co-stimulation of axons originating from ganglion cells of the outer regions (Rattay, F., "Effective electrode configuration for selective stimulation with inner eye prostheses", *IEEE Trans Biomed Eng.*, 2004 September; 51(9):1659-64.) Nanowire ridges 138, on the order of 5 µm-400 µm in length and having widths corresponding to the thickness of the nanowires (50 nm to 1 µm), can be formed using processes similar to those described above. Photolithography can then be used to pattern electrodes 140 in different shapes and sizes for selective line stimulation. Such stimulation sites would cover an area along the nanowires. The ridges can be tapered or have sharp edges.

Figure 15:
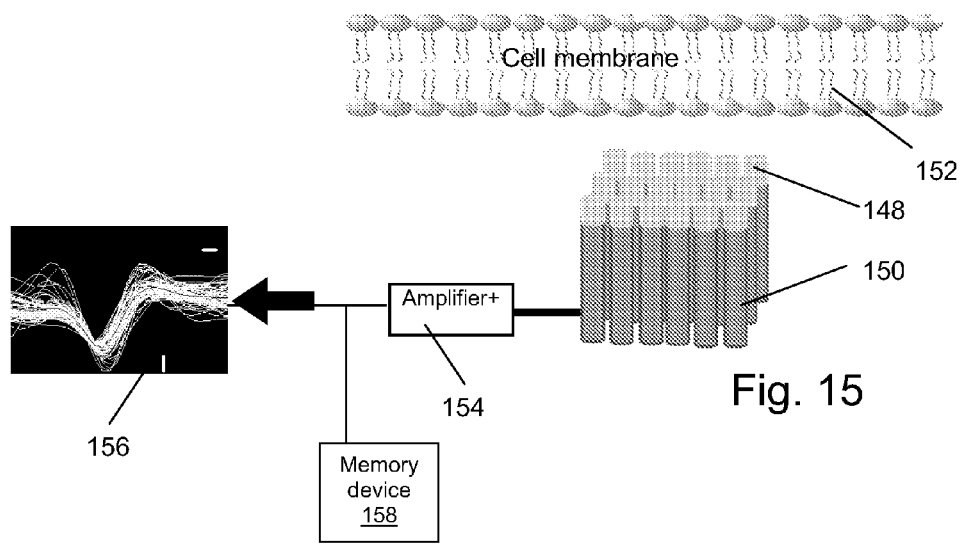
FIG. 15 is a diagram showing use of the inventive nanowire platform for recording extracellular or intracellular potential from a neuron.

The inventive nanowire platform can be used for recording action potentials from neurons extracellularly and intracellularly. The recording can be improved by using any of the following materials on the tips of the nanowires, including stainless steel, tungsten, platinum, platinum-iridium alloys, iridium oxide, titanium nitride, and poly(ethylenedioxythiophene) (PEDOT). The deposited material can connect one or a bundle of nanowires to one lead, which is also made of the same material. A basic neuroamplifier circuit 154 can be used to condition and amplify the recorded action potential. This recording potential can be combined with the stimulation in an implant. FIG. 15 provides an example of the nanowire platform can be used to record extracellular or intercellular potential from a neuron. The nanowires 150, with enhanced tips 148, may be positioned near a neuron in a slice, animal or cell culture model (cell membrane 152 is shown). Basic circuitry, design of which will be readily apparent to those of skill in the art, will be included to condition and amplify the acquired signal. Display 156 illustrates an example of the acquired signal. The resulting signal may be stored in a memory device 158.

The nanowire platform of the present invention may be used as an interface and potential prosthesis to generate a nanoscale molecular signaling cue or stimulation based on electric currents for the induction of chemically secreted neuroprotective factors from cells, i.e., not just neurons, but glial cells and other central and peripheral nervous system cells.

In one example, nanowire arrays may be engineered into a broader device to act as an electrical-to-chemical transducer in the development of a nanoengineered artificial chemical synapse. The nanowires may be configured to respond to light or some other input signal. In response to detection of such an input, the array may use its electrical properties to trigger the release of chemically-based signaling molecules, such as various classes of neurotransmitters (e.g., peptides or catecholamines) from a thin film, polymer, or other synthetically engineered material. In one example, a synthetic neurotransmitter may encapsulated within cells or layers in a membrane formed from an electroactive polymer into which the nanowire electrodes extend. The membrane, when activated, opens the cells (or pores in the layers) for a sufficient duration to release the appropriate quantity of the neurotransmitter to effect the desired change. The released molecules can then chemically stimulate and signal neurons, thus inducing or mimicking synaptic behaviors. Nanowire-based devices of this type may be useful for treatment of a wide range of conditions involving synaptic dysfunction or failure, including but not limited to, depression, Alzheimer's disease, Parkinson's disease, and may even be useful in treating drug addiction and some forms of paralysis.

Figure 16:
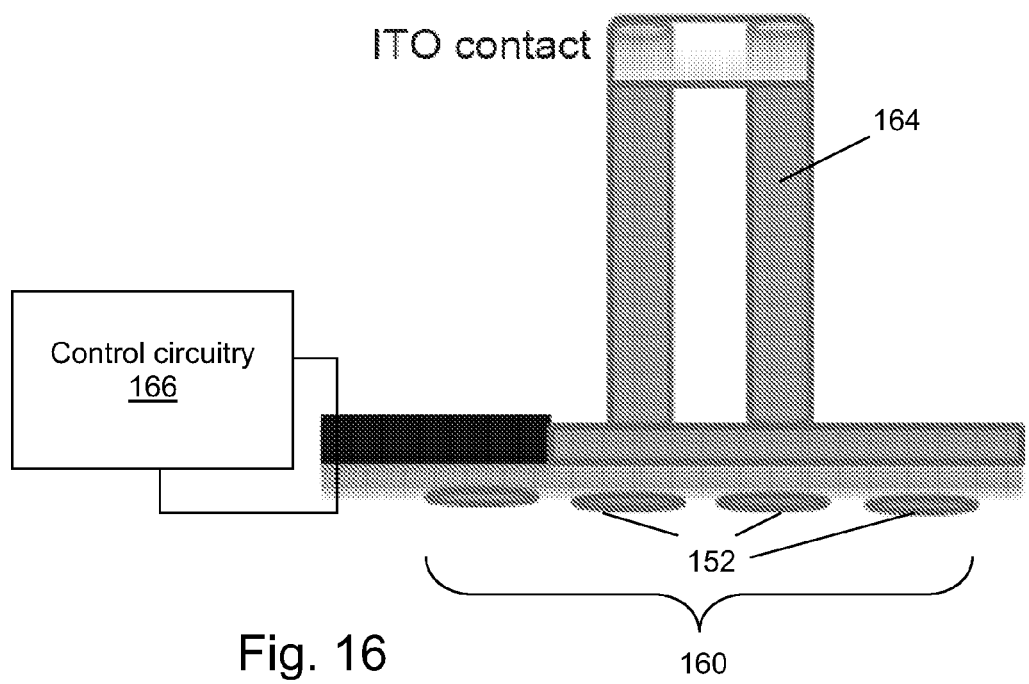
FIG. 16 is a diagrammatic view of a nanoimager with individually addressable nanowires.

In still another application of the inventive nanowire platform, individually addressable nanowires, or bundled nanowires, as shown in FIG. 16, can be used as an imager array for a retinal prosthesis. In this application, the nanowires would not be in contact with the cells in the retina. Instead, a device with stimulating electrodes, in the form of a microelectrode array (MEA) 160 fabricated from a flexible material (PDMS, PARYLENE™ or polyimide), may be placed in the subretina or epiretina and connected to the nanoimager. An inductive link, similar to that described above (not shown here), can be used to power the device. The flexible MEA 160 can have electrodes 152 with diameters ranging from 100 µm to 1 µm formed using materials including platinum, platinum-iridium alloys, iridium oxide, titanium nitride, and poly(ethylenedioxythiophene) (PEDOT). Photocurrent produced by the bundled or individually-addressable nanowires 164 can be sent into the stimulation electrodes 152. Additional circuitry 166 can be added to fine tune the output of the nanowires before it is sent to the MEA. The conditioning involves control over waveform shape, height and duration.

In addition to its application as a retinal prosthesis, the molecular scale of the inventive nanowire platform makes it broadly applicable as an interface and potential prosthesis for other sensory systems and non-sensory parts of the brain and central nervous system.

REFERENCES (INCORPORATED HEREIN BY REFERENCE.)

1) Kim, H., et al., "Fabrication of Vertical Silicon Nanowire Photodetector Arrays using Nanoimprint Lithography", *Proceedings of SPIE*, 2010, pp. 7591-7595.
2) Soci, C., et al., "ZnO Nanowire UV Photodetectors with High Internal Gain", *Nano Letters*, 2007, Vol. 7, p. 1003.
3) Zhang, A., et al., "Silicon Nanowire Detectors Showing Phototransistive Gain", *Applied Physics Letters*, 2008, Vol. 93, 121110-1-3.
4) Khraiche, M. L., N. Jackson, and J. Muthuswamy. Biology Society, 2009. *EMBC 2009. Annual International Conference of the IEEE*, 2009.
5) Humayun, M. S., et al., "Visual perception in a blind subject with a chronic microelectronic retinal prosthesis", *Vision Res.*, 2003, 43(24), pp. 2573-2581.
6) Winter, J. O., et al., "Retinal prostheses: current challenges and future outlook", *Journal of Biomaterials Science, Polymer Edition*, 2007, 18, pp. 1031-1055.
7) Besch, D., et al., "Extraocular surgery for implantation of an active subretinal visual prosthesis with external connections: feasibility and outcome in seven patients ",. *Br. J. Ophthalmol*, 2008, 92(10): p. 1361-8.
8) Zhang, A., et al., "Nanowire Photodetectors", *Journal of Nanoscience and Nanotechnology*, 2010, 10: p. 1430-1449.
9) Zhang, A., et al., "Characterization and physics of topdown silicon nanowire phototransistors", *Proceedings of SPIE*, 2010, 7608, p. 76081D-8.
10) Sun, K., et al., "Compound Semiconductor Nanowire Solar Cells" *Selected Topics in Quantum Electronics, IEEE Journal of*, 2010. PP(99): p. 1-17.
11) Soci, C., et al., *Nanowire Photodetectors*. Journal of Nanoscience and Nanotechnology, 2010, 10(3): p. 1439-1449.
12) Curcio, C. A., et al., "Human photoreceptor topography", *J Comp Neurol*, 1990, 292(4): p. 497-523.
13) Friedburg, C., M. M. Thomas, and T. D. Lamb, "Time course of the flash response of dark- and light-adapted human rod photoreceptors derived from the electroretinogram", *J Physiol*, 2001. 534(Pt 1): p. 217-42.
14) Palanker, D., et al., "Design of a high-resolution optoelectronic retinal prosthesis", *J Neural Eng*, 2005, 2(1): p. S105-20

The invention claimed is:
1. An implantable device comprising:
an array of silicon nanowires having a predetermined spatial distribution, density, size and shape, each nanowire having a first end and a second end, the array of nanowires configured to be implanted within a tissue for receiving a triggering signal;
an electrical conductor disposed at a the first end of all nanowires in the array of nanowires;
a bias source in electrical communication with the electrical conductor for biasing the array; and
an electrode disposed on a the second end of each nanowire to define a plurality of electrodes, wherein each nanowire produces a current at a corresponding electrode in response to detection of the triggering signal, wherein the array of nanowires generates an output signal corresponding to the currents produced in response to the triggering signal.

2. The implantable device as in claim 1, wherein the triggering signal comprises light impinging on the tissue and the output signal comprises a signal for stimulating release of a neutrotransmitter by one or more photoreceptor neurons.

3. The implantable device as in claim 1, further comprising a recording device comprising an amplifier and a memory device, wherein the wherein the output signal is communicated to the recording device for amplification and storage in the memory device.

4. The implantable device as in claim 1, further comprising an electrically-reactive membrane having a plurality of openable cells for retaining a neurotransmitter, wherein the electrically-reactive membrane is in electrical contact with the plurality of electrodes, and wherein the output signal activates the electrically-reactive membrane to release at least a portion of the neurotransmitter in response to detection of the signal.

5. The implantable device of claim 1, wherein each nanowire has a diameter ranging between 10 nm-5 µm and a height ranging between 1-50 µm.

6. The implantable device of claim 1, wherein a spacing between nanowires in the array is 2 nm or greater.

7. The implantable device of claim 1, wherein the array of nanowires includes a plurality of nanoridges having lengths of approximately 5 µm to 400 µm, each nanoridge having a plurality of stimulation electrodes disposed along its length for selectively activating local ganglion cells.

8. The implantable device of claim 1, wherein the array of nanowires is disposed on a flexible substrate comprising a biocompatible material.

9. The implantable device of claim 8, wherein the biocompatible material is poly(p-xylylene) or polydimethylsiloxane.

10. The implantable device of claim 1, wherein spaces between the nanowires in the array of nanowires are filled with a biocompatible material.

11. The implantable device of claim 10, wherein the biocompatible material has channels formed therethrough, the channels adapted to pass nutrients to the tissue.

12. The implantable device of claim 10, wherein the biocompatible material is poly(p-xylylene) or polydimethylsiloxane.

13. An implantable device for detecting an electrical potential within a tissue and generating an output therefrom, the device comprising:

an array of silicon nanowires;

an electrical conductor disposed at a first end of all nanowires in the array of nanowires;

a bias source in electrical communication with the electrical conductor for biasing the array;

a plurality of electrodes disposed on a second end of each nanowire in the array of nanowires, wherein one or more pairs of nanowires, when implanted within tissue, detects an intracellular or extracellular action potential within the tissue and generates an output signal at the electrical conductor; and a recording device comprising an amplifier connected to the electrical conductor for receiving and storing a signal corresponding to an amplified intracellular or extracellular action potential.

14. The implantable device as in claim 13, further comprising an electrically-reactive membrane having a plurality of openable cells for retaining a neurotransmitter, wherein the electrically-reactive membrane is in electrical contact with the electrical conductor, and wherein the output signal further activates the electrically-reactive membrane to release at least a portion of the neurotransmitter in response to detection of light.

15. The implantable device of claim 13, wherein the array of nanowires is disposed on a flexible substrate comprising a biocompatible material.

16. The implantable device of claim 15, wherein the biocompatible material is poly(p-xylylene) or polydimethylsiloxane.

17. The implantable device of claim 13 wherein spaces between the nanowires in the array of nanowires are filled with a biocompatible material.

18. The implantable device of claim 17, wherein the biocompatible material has channels formed therethrough, the channels adapted to pass nutrients to the tissue.

19. The implantable device of claim 1, wherein multiple nanowires within the array of nanowires correspond to a single electrode.

20. The implantable device of claim 13, wherein multiple nanowires within the array of nanowires correspond to a single electrode.

* * * * *